(12) United States Patent
van Dijk et al.

(10) Patent No.: US 6,667,055 B2
(45) Date of Patent: Dec. 23, 2003

(54) FILLER BINDER FOR TABLETS

(75) Inventors: Gerard Johan van Dijk, Roosendaal (NL); Anko Cornelus Eissens, Delfzijl (NL); Henderik Willem Frijlink, Eelde (NL); Aart Pieter Cornelis Olivier, Roosendaal (NL); Gerad Klaas Bolhuis, Uithuizermeeden (NL)

(73) Assignee: Cooperatie Cosun U.A., Breda (NL)

( * ) Notice: Subject to any disclaimer, the term of this patent is extended or adjusted under 35 U.S.C. 154(b) by 0 days.

(21) Appl. No.: 10/013,338

(22) Filed: Dec. 10, 2001

(65) Prior Publication Data

US 2002/0192278 A1 Dec. 19, 2002

Related U.S. Application Data

(63) Continuation of application No. PCT/NL00/00401, filed on Jun. 9, 2000.

(30) Foreign Application Priority Data

Jun. 11, 1999 (EP) .............................. 99201865

(51) Int. Cl.[7] ............................ A61K 9/14; A61K 9/16; A61K 9/20

(52) U.S. Cl. ........................ 424/464; 424/465; 424/489; 514/951; 514/961

(58) Field of Search ................................ 424/489, 441, 424/466, 465, 464, 468

(56) References Cited

U.S. PATENT DOCUMENTS 5,064,501 A * 11/1991 Boersen ..................... 159/4.08
5,626,876 A * 5/1997 Muller et al. ............... 424/484

FOREIGN PATENT DOCUMENTS

| EP | 0376337 | | 7/1990 | |
|---|---|---|---|---|
| JP | 59065322 | * | 11/1985 | ........... C07B/57/00 |
| JP | 08113541 A | * | 5/1996 | ........... C07B/57/00 |

* cited by examiner

*Primary Examiner*—James M. Spear
(74) *Attorney, Agent, or Firm*—Banner & Witcoff, Ltd.

(57) ABSTRACT

The invention relates to a novel filler-binder for tablets, which shows a significantly reduced lubricant sensitivity when compared to prior art filler-binders. The invention further relates to a process of making said filler-binder and to the tablet obtainable by said process.

14 Claims, 4 Drawing Sheets

FILLER BINDER FOR TABLETS

This application is a continuation of PCT/NL00/00401 filed Jun. 9, 2000

BACKGROUND OF THE INVENTION

1. Field of the Invention

The invention relates to a novel filler-binder for tablets, a process for making tablets using said filler-binder and to tablets obtainable by said process.

2. Description of the Related Art

The production of tablets by direct compaction has for many years been a growing field in the pharmaceutical industry and other areas, such as tabletting of detergents. Many excipients with special advantages in the direct compaction process have been developed and applied in the past decades. Especially in the class of the filler-binders, many new excipients as well as many new physical forms of existing excipients have entered the market. For an overview of such excipients, reference is made to G. K. Bolhuis and Z. T. Chowhan, 'Materials for direct compaction', in 'Pharmaceutical compaction technology', Eds. G. Alderborn and C. Nyström, Marcel Dekker, Inc., New York, 1996, pp. 419–500.

Because the ingredients for the tablets are usually only dry-mixed before compression, the characteristics and performance of the filler-binder are essential for the quality attributes of the final tablet. Typical examples of direct compaction filler-binders are the free flowing physical forms of lactose (spray dried or agglomerated), mannitol, microcrystalline cellulose, sorbitol, sucrose (compressible sugar), or inorganic salts. Each of these is available in different physical forms having their respective advantages in the direct compaction process.

To perform as a suitable filler-binder, an excipient should meet a number of requirements. The compactibility should be high to ensure that the tablet meets the usual requirements on crushing strength and friability. Further, a good flowability and good blending properties are needed in order to ensure mass (and content) uniformity of the tablet. Inertness of the excipient is necessary in order to avoid interaction with the drug or other active substance present in the tablet, or with any other excipient. A filler-binder should moreover be stable during storage under different conditions. Both as raw material and when present in the tablet, its physico-chemical properties should remain substantially unchanged over time. Also, a filler-binder should be non-toxic and accepted by regulatory authorities, preferably it is described in pharmacopeia. In addition, a filler-binder preferably has a high batch to batch reproducibility with respect to the physico-chemical quality of the product. Finally, other requirements may relate to the effect of the filler-binder on the disintegration and drug release, price and the world-wide availability of the material.

A great disadvantage of the known filler-binders is that they are very sensitive to the presence of lubricants, particularly when tablets are produced using high speed tabletting machines as is being done in the pharmaceutical industry.

Lubricants are substances incorporated into tablets for prevention of adhesion between the tablet (to be) formed and the equipment used for its formation, such as punches and dies or other parts of a press used for compaction, and the like. Examples of compounds that are regularly used as lubricant in this respect are fatty substances, such as magnesium stearate, sodium stearylfumarate, glycerylbehenate, glyceryl monostearate, calcium stearate, hydrogenated vegetable oil, polyethylene glycol, talc, and zinc stearate. It is believed that the lubricant partially or completely coats the filler-binder particles. Thus, due to the presence of the lubricant, particularly after compaction has been carried out, the surface area of the filler-binder particles that is in direct contact with other filler-binder particles is significantly reduced, leading to a significantly reduced binding capacity of the filler-binder. This effect is particularly apparent in the case of filler-binders that show plastic deformation upon compaction. However, said effect also occurs, although to a lesser degree, with filler-binders that are brittle and fragment upon compaction.

SUMMARY OF THE INVENTION

The present invention aims to provide a filler-binder for tablets that shows a reduced lubricant sensitivity when compared with the prior art filler-binders. Of course, the filler-binders should meet many, if not all, of the criteria mentioned above, so that it is suitable for use as a filler-binder in tablets.

Surprisingly, it has now been found that when a filler-binder has a specific morphology, its sensitivity in binding capacity to a lubricant in a tablet is significantly reduced. The desired effect is achieved when the filler-binder consists of particles, which are hollow. Thus, the invention relates to a filler-binder for a tablet in the form of hollow particles.

DETAILED DESCRIPTION OF THE INVENTION

Figure 1:
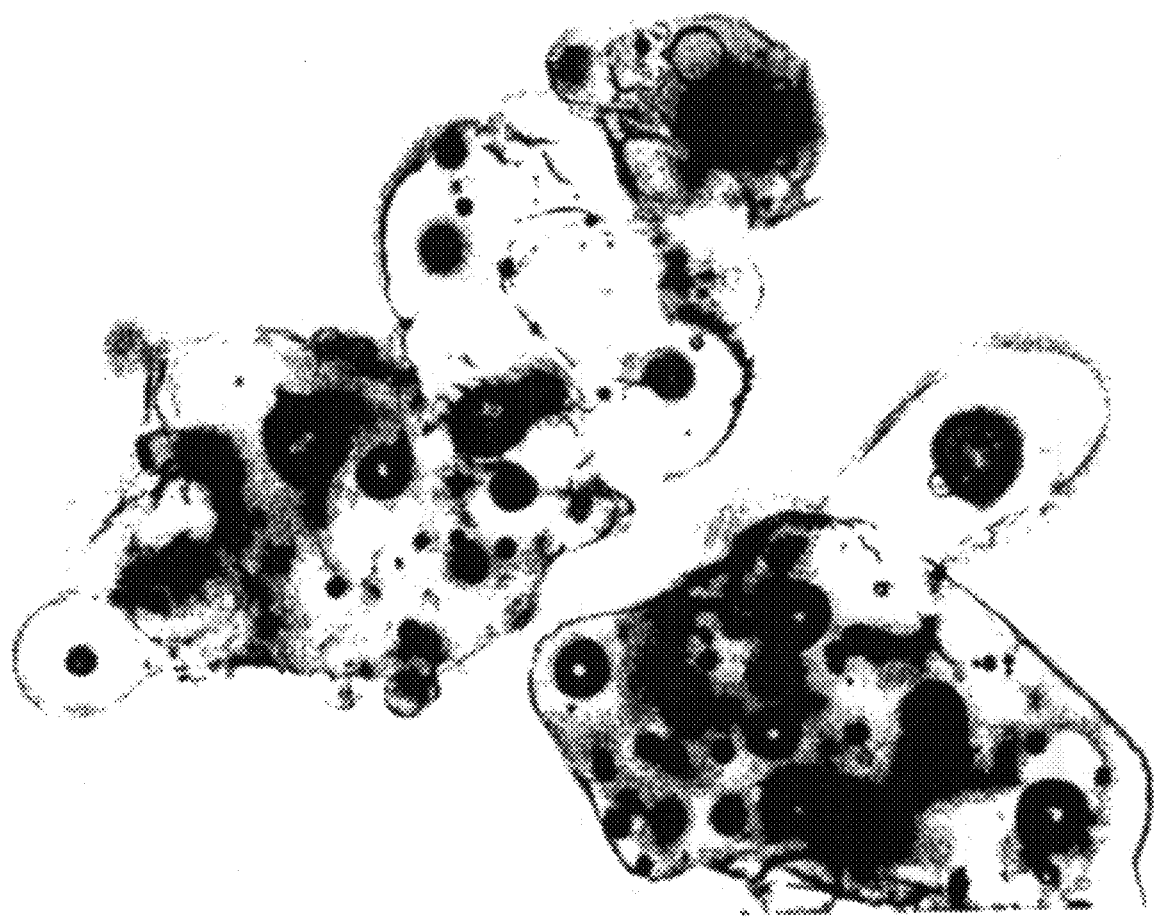
FIG. 1 depicts light microscopy of powder samples dispersed in paraffin oil showing agglomerates having a porous structure without large vacuoles (400×magnification).

In accordance with the invention, the term 'hollow particle' refers to particles, preferably in the form of a sphere or in sphere-like form, which comprise a relatively large space inside them, filled with heterogeneous material (i.e. different from the material of the filler-binder). Usually, this heterogeneous material will be an (inert) gas, such as air or nitrogen. The outer shell of the particles, defining said space, may be porous or non-porous. The volume of the space is preferably at least 10%, more preferably at least 25%, even more preferably at least 35% of the total volume of the particles. Accordingly, the true density (which may be measured using pycnometry) of the present particulate filler-binder is much smaller than the density of the same materials not having the specific morphology of the invention. Typically, the density will be only 90% or less, preferably only 85% or less, of the true density of the same material in crystalline form or when the material is milled to destroy the hollow structure.

The mean size (diameter) of the particles is not very critical and may be chosen in the usual range for filler-binders, which is from 25 to 1000 μm, preferably from 50 to 200 μm. The particle size distribution is preferably narrow, e.g. between 25 and 50 μm, more preferably between 63 and 240 μm. In this regard, the term particles size distribution implies that at least 80% of the particles has a size within the specified ranges. The particle size and particle size distribution can conveniently be determined using scanning electron microscopy or methods such as sieving of laser diffraction measurements.

In a preferred embodiment, additional functionality of the filler-binder may be created by forming agglomerates of the hollow particles. The formation of agglomerates has been found to have a very beneficial effect on the flow properties of the filler-binder. The agglomerates may be formed using any known technique, for instance as has been described in the Handbook of Powder Technology, vol. 1, Particle Size Enlargement, Eds. J. C. Williams and T. Allen, Elsevier Scientific Publishing Company, 1980. Preferably, the agglomerates consist of between 2 and 10 particles.

In principle, any material that is conventionally used as a filler-binder in tablets, and thus meets the above mentioned criteria for filler-binders, is suitable to be used as filler-binder according to the invention, as long as said material may be formed into the specific morphology as defined above. Accordingly, it is desired that the material is soluble in water. Preferably, the solubility in water is at least 1:100 (w/w), more preferably at least 1:10, even more preferably at least 1:1 (w/w). Further, when an increasing amount of air is included in the particles of the material, the tendency of the particles to exhibit fragmentation under compression preferably increases, which in turn results in a higher crushing strength and a decrease in lubricant sensitivity. In addition, it is preferred that the material has a relatively high glass transition temperature. In this regard, a high glass transition temperature is meant to be at least 50° C., preferably at least 70° C.

Examples of suitable materials that may be used as filler-binder may be found in G. K. Bolhuis and Z. T. Chowhan, 'Materials for direct compaction', in 'Pharmaceutical compaction technology', Eds. G. Alderborn and C. Nyström, Marcel Dekker, Inc., New York, 1996, pp. 419–500. Important classes of materials in this regard are inorganic salts, such as calcium phosphates, calcium carbonate, kaolin, mono- or disaccharides or polyols, such as mannitol, sorbitol, lactose, lactitol, dextrose, fructose, xylitol and sucrose, polysaccharides, such as (microcrystalline) cellulose, starch, pregelatinized starch or dextrins. Preferably, a saccharide, more preferably a polysaccharide, is used. Particularly good results have been obtained by using a fructan.

A fructan is understood to mean any oligo- or polysaccharide that contains a plurality of anhydrofructan units. The fructans can have a polydisperse chain length distribution and can have a linear or branched chain, the latter of which are sometimes referred to as glucans. Accordingly, in the context of the invention the term fructan is intended to include glucans. Preferably, the fructans contain mainly β-1,2 bonds, as in inulin, but they may also contain β-2,6 bonds, as in levan. Suitable fructans can originate directly from a natural source, but may also have undergone a modification. Examples of modifications in this connection are reactions, known per se, which lead to a lengthening or shortening of the chain length. Suitable fructans have an average chain length (degree of polymerization, DP) of at least 2, up to about 1,000. Preferably, a fructan is used having a degree of polymerization of at least 3, more preferably at least 6, most preferably at least 10, up to about 60.

Fructans suitable for use in accordance with the invention include, in addition to naturally occurring polysaccharides, industrially prepared polysaccharides, such as hydrolysis products, which have shortened chains, and fractionated products having a modified chain length, in particular a chain length of at least DP 10. A hydrolysis reaction for obtaining a fructan having a shorter chain length can be carried out enzymatically (for instance with endoinulinase), chemically (for instance with aqueous acid), physically (for instance thermally) or by the use of heterogeneous catalysis (for instance with an acid ion exchanger). Fractionation of fructans, such as inulin, can be accomplished, for instance, by crystallization at low temperature, separation with column chromatography, membrane filtration, and selective precipitation with an alcohol. Other fructans, such as fructans having a long chain, can be obtained, for instance, by crystallization, from fructans from which mono- and disaccharides have been removed, and fructans whose chain length has been enzymatically extended can also be used. Further, reduced fructans can be used. These are fructans whose reducing terminal groups, normally fructose groups, have been reduced, for instance with sodium borohydride or hydrogen in the presence of a transition metal catalyst. Also eligible for use are fructans which have been chemically modified, such as crosslinked fructans and hydroxyalkylated fructans.

In a preferred embodiment, the fructan which may be used according to the invention is inulin or a derivative thereof. Inulin is an inert and stable material, is essentially non-reducing and shows only moderate hygroscopicity. The use of inulin is considered safe, when administered orally or parenterally; it is described in monographs in a number of pharmacopeia, such as the USP and BP and is therefore acceptable to most regulatory authorities. Further, inulin shows a good physical stability, both in its amorphous and in its crystalline state. The length of the fructose chain can be used to vary its compression characteristics. Furthermore, inulin can be used as a low calorie sweetener, without the risk of caries.

Inulin is a polysaccharide consisting of β-1,2 bound fructose units with an α-D-glucopyranose unit at the reducing end of the molecule. The substance occurs inter alia in the roots and tubers of plants of the Liliaceae and Compositae families. The most important sources for the production of inulin are Jerusalem artichoke, dahlia and chicory root. In the industrial production of inulin, the starting material is mainly chicory root. The principal difference between inulins originating from the different natural sources resides in the degree of polymerization, which may vary from about 6 in Jerusalem artichokes to 10–14 in chicory roots and higher than 20 in dahlias.

The above materials may be formed into the specific morphology as required by the invention by any suitable method. Examples of such methods are described in the 'Spray Drying Handbook', K. Masters, $5^{th}$ ed., Longman Scientific & Technical Publishers, 1991, pp. 329–337 and 346–349, which is incorporated herein by reference. The person skilled in the art will be able to design suitable spray drying methods for obtaining the desired morphology on the basis of his expert knowledge and the disclosure in said reference.

The formation of hollow particles by spray drying may be performed as follows, illustrated by reference to inulin, which is not to be regarded as restricting the scope of the invention. An aqueous solution or suspension of inulin, comprising between 20 and 50 wt. % of inulin, is fed into a spray drying apparatus at a temperature between 5 and 100°

C., and atomized, e.g. by use of a rotating wheel or one or more pressure nozzles. The feed temperature, as well as the humidity, may be employed to adjust the crystallinity of the material. A low temperature will lead to a more crystalline product, whereas a high temperature leads to a more amorphous product. In this manner, the brittleness and solubility (which may be considered a measure for the disintegration time of a tablet in vivo) may be controlled. Drying air of a temperature between 150 and 250° C., inter alia depending on the stability of the particulate material (in casu inulin) is introduced in the spray drying apparatus at or near the atomizing part of the device. The temperature of the outgoing air of the spray dryer is preferably set between 80 and 120° C. If desired, the spray dried product may be dried further, e.g. in an external, vibrating fluidized bed with air of 80–120° C., and cooled, e.g. in an external, vibrating fluidized bed with air of ambient temperature.

The liquid to be spray dried, i.e. the aqueous solution or suspension mentioned above, should contain a sufficient amount of a gas in order to produce the hollow structure of the particles. The amount of gas present may be controlled by controlling the pressure of the gas. In a preferred embodiment, the gas is carbon dioxide, in which case the liquid preferably does not contain a buffer. The absence of a buffer allows the solubility, and thus the amount present, of the gas to be determined chemically. This type of spray drying, wherein a gas is employed, has been referred to as foam spray drying in the literature where it is suggested for use in the preparation of sweetening compositions. In this regard reference is made to inter alia the European patent applications 0 334 617, 0 387 950, and 0 861 852, which disclose details for carrying out the foam spray drying procedure that may also be useful in the context of the present invention.

The present filler-binder may be used in the production of tablets in any suitable manner, for instance such as has been described in 'Pharmaceutical compaction technology', Eds. G. Alderborn and C. Nyström, Marcel Dekker, Inc. New York, 1996, pp. 419–500, or 'The Pharmaceutical Codex', Ed. W. Lund, The Pharmaceutical Press, London, 1994. In the context of the present invention, the term tablet is intended to encompass various oral dosage forms, such as uncoated tablets, effervescent tablets, dispersible tablets, gastro-resistant tablets, modified-release tablets, tablets for use in the mouth, chewable tablets, lozenges, boluses, caplets or capsules and tablets for other than oral routes of administration such as molded tablets, vaginal tablets, tablets for rectal use, hyperdermic tablets and implants.

In order to produce the tablets, the filler-binder as described above will be mixed with the other desired ingredients of the tablet, such as lubricants, active ingredients, flavoring agents and the like. The active ingredient may be any type of substance the administration of which may be accomplished by use of tablets. Examples include drugs, food supplements, such as vitamins, and other types of active ingredients that can be administered to a patient orally or by any other suitable route, such as rectally or by implantation, in the form of a tablet. The flavoring agent may be any non-toxic substance that imparts an agreeable taste to the tablet, so that the intake of the tablet is more acceptable to patients. Examples include sweeteners, herbs and spices, synthetic flavoring agents and the like. The lubricant may be any substance that can suitably be incorporated into a tablet for prevention of adhesion between the tablet (to be) formed and the equipment used for its formation, such as an extruder, a mold, a press, and the like. Examples of compounds that are regularly used as lubricant in this respect are fatty substances, such as magnesium stearate, sodium stearylfumarate, glycerylbehenate, glyceryl monostearate, calcium stearate, hydrogenated vegetable oil, polyethylene glycol, talc and zinc stearate.

Tablets may be produced by wet granulation techniques and by direct compaction of powder mixtures. Preferably, the tablets are produced by way of compaction (i.e. the use of high pressure) of the dry mixture obtained after mixing the desired ingredients. Examples of suitable compaction methods include extrusion, compression, milling, and the like. Preferably, use is made of a (high speed) tabletting machine.

The invention will now be elucidated by the following, non-restrictive examples.

EXAMPLES

Materials and Methods

Three inulin products and one lactose product were investigated. Sample A was a commercially available product, viz. Frutafit® IQ from Sensus, Roosendaal, The Netherlands, which consisted more or less of agglomerated particles.

Sample B was prepared from Frutafit® EXL (inulin from chicory, Sensus, Roosendaal, The Netherlands). A 25 wt. % solution of this material in water was crystallized by cooling to 5° C. and the resulting suspension of this material was, after saturation with air by mechanically stirring with air intake, fed at pH 4.9 and 5° C. into a spray dryer (Anhydro®, water evaporation capacity 1200 kg/hr) and atomized by means of four high pressure nozzles at 150–165 bar (conditions: temperature of ingoing air: 215° C.; temperature of outgoing air: 100° C.). Final drying and cooling of the powder leaving the spray dryer was carried out using vibrating fluidized beds with air; starting at 100° C. and cooling to ambient temperature. Fines were separated from the outgoing air by cyclones and reintroduced into the spray cloud formed by the nozzle assembly resulting in an agglomerating effect.

Sample C was prepared from demineralized inulin thin juice extracted from fresh chicory. The thin juice was concentrated by evaporation to a 30 wt. % solution, saturated with air by mechanically stirring with air intake and fed at pH 5.0 and 90° C. into a spray dryer (Anhydro®,water evaporation capacity 1500 kg/hr) and atomized by means of a rotary atomizer (conditions: temperature of ingoing air: 195°; temperature of outgoing air: 98° C.). Cooling of the powder leaving the spray dryer was carried out using a vibrating fluid bed with air at ambient temperature.

Sample D was prepared from Lactopure® (Domo Food Ingredients, Beilen, The Netherlands), a low ash edible lactose monohydrate. A 30 wt. % solution in demineralized water was gassed with carbon dioxide and fed at 60° C. into a spray dryer (Niro Mobile minor, water evaporation capacity 1 kg/hr) and atomized by means of a two fluid nozzle with air (conditions: temperature of ingoing air: 135° C.; temperature of outgoing air: 65° C.). The powder was separated with a cyclone from the outgoing air-powder mixture.

In table 1 the physico chemical properties of the samples are described.

Magnesium stearate (Ph.Eur.) was supplied by Centrachemie, Etten-leur, The Netherlands. Sodium starch glycolate (Ph. Eur.) was obtained from AVEBE, Veendam, The Netherlands The flow properties were determined by measurement of the minimum aperture through which the material was still flowing (funnel flow).

The moisture content was determined in about 3 g inulin, using an infra-red drying balance (Sartorius MA 40), after drying at 105° C.

The density was determined using helium pycnometry (Quantasorb multipycnometer). The sample, as it was obtained, was measured to obtain information on the amount of included air in the particles. After milling a true density of 1.48 g/cm$^3$ was found for inulin and 1.54 g/cm$^3$ for lactose monohydrate.

Bulk density was determined by pouring the powder (about 50 g) in a calibrated glass cylinder. Tap density was determined after tapping the cylinder for two hundred times.

Particle size distribution was measured by laser diffraction (Mastersizer, Malvern Instruments).

TABLE 1

Physico-chemical characteristics

| Batch Number | Mean DP | Amorphous/ Crystalline | Moisture content | Particle size [μm] D (v, 0.1) | D (v, 0.5) | D (v, 0.9) | Monosaccharides* | Disaccharides |
|---|---|---|---|---|---|---|---|---|
| A | ~10 | Amorphous | 2.7% | 23 | 56 | 102 | 5.8% | 5.8% |
| B | 24 | Crystalline | 4.1% | 58 | 105 | 169 | <0.1% | <0.1% |
| C | ~10 | Amorphous | 2.8% | 16 | 46 | 91 | 3.5% | 4.1% |
| D | 2 | Amorphous | 3.5% | 11 | 35 | 89 | — | 100% |

*: sum of glucose and fructose

Flat faced tablets of 500 mg and a diameter of 13 mm were prepared on a programmable hydraulic press (ESH testing, Brierly Hill, UK) at different compression forces. The speed of the upper punch was 300 mm/s. The high speed of the upper punch was chosen in order to simulate high speed tabletting machines. The tablets were prepared of the pure sample (unlubricated) or after mixing the inulin with 0.5% magnesium stearate for 2 minutes in a Turbula mixer (model 2 P, W. A. Bachofen, Basel, Switzerland) at 90 RPM (lubricated). For one experiment 4% sodium starch glycolate was added to the formulation too.

The tablet strength was determined (at least 30 minutes after compaction) with a Schleuniger 4 M tester (D. Schleuniger, Solothurn, Switzerland), the presented results are the mean of 3 measurements. The lubricant sensitivity ratio (L.S.R.) was calculated from the crushing strength of lubricated and unlubricated tablets. The porosity of the tablets was calculated from the tablet dimensions and the true density of the inulin or the lactose monohydrate. The disintegration times were determined using the Ph.Eur. apparatus without disks. The presented data are the mean value of 6 measurements.

The friability of the tablets was determined in the Roche friabilator single blade apparatus according to the Ph.Eur.

Results and Discussion

Properties of the Raw Materials

In table 2 the flow properties of the different inulin types are given. The results clearly show that the flow properties of sample B was sufficient for a direct compaction process. Samples A, C and D had a relatively poor flowing behavior. In general, the flow properties clearly reflect the differences in particle size of the different batches.

Figure 2:
FIG. 2 depicts light microscopy of powder samples dispersed in paraffin oil showing agglomerates made up of single particles with large vacuoles (400×magnification).
Figure 3A:
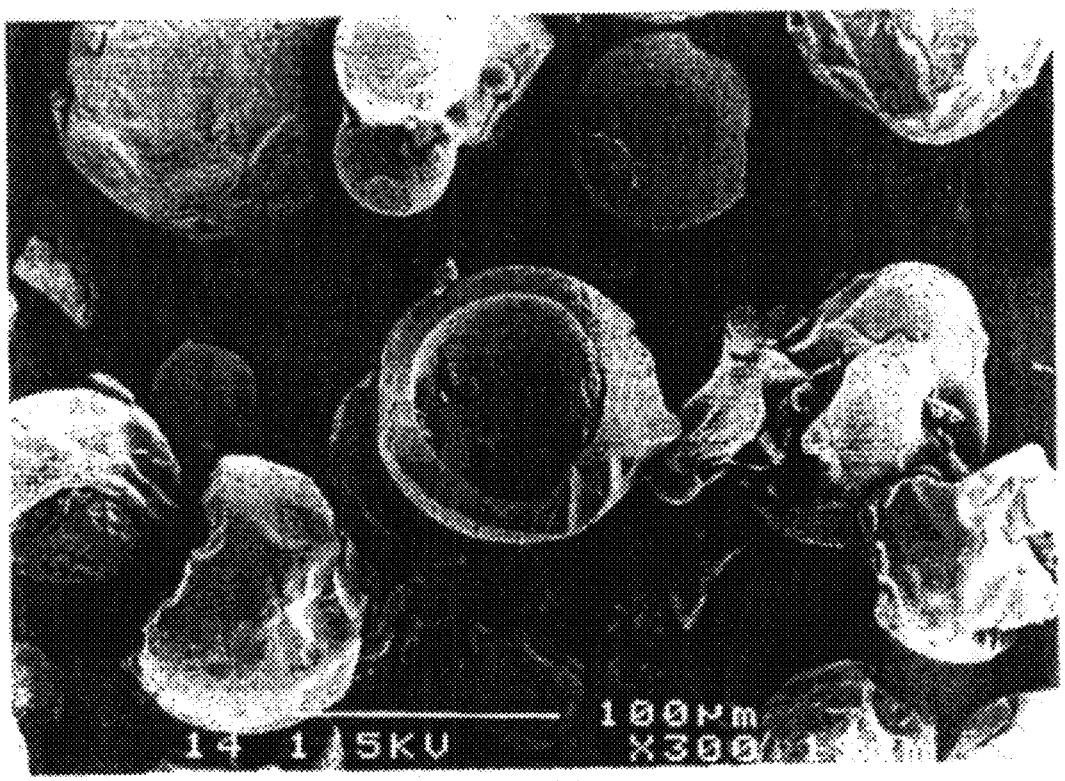
FIGS. 3A–3B depict scanning electron micrographs of powder samples dispersed in paraffin oil at 300× magnification (3A) and 2000×magnification (3B).
Figure 3B:
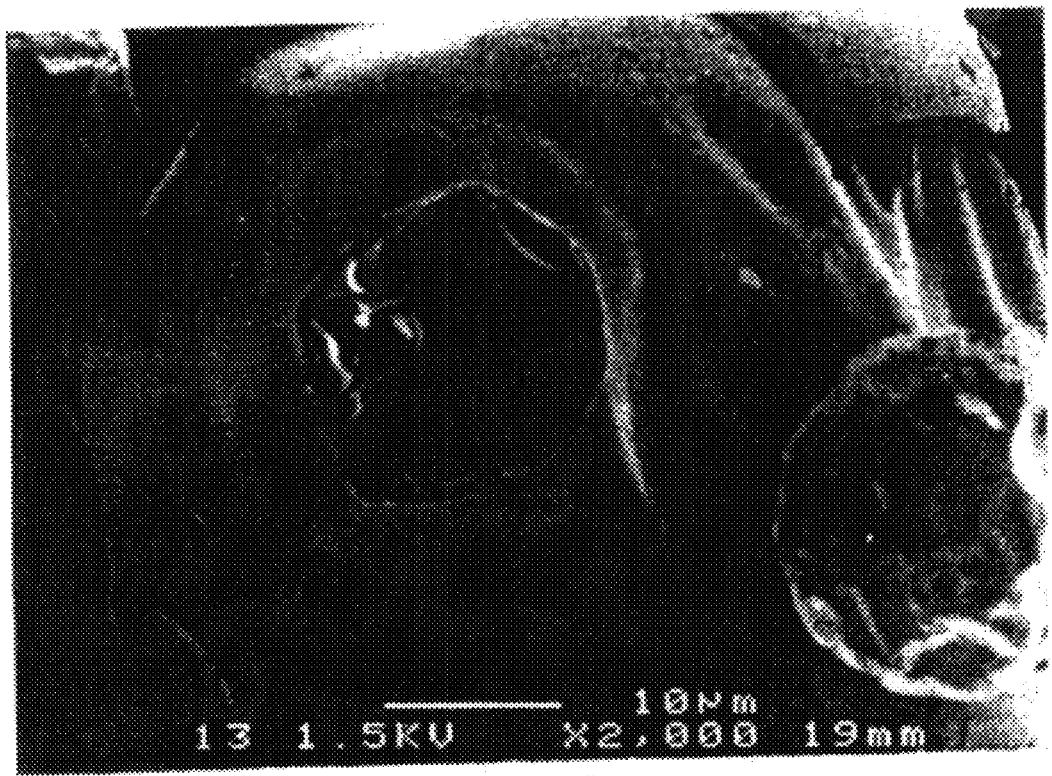
Figure 4A:
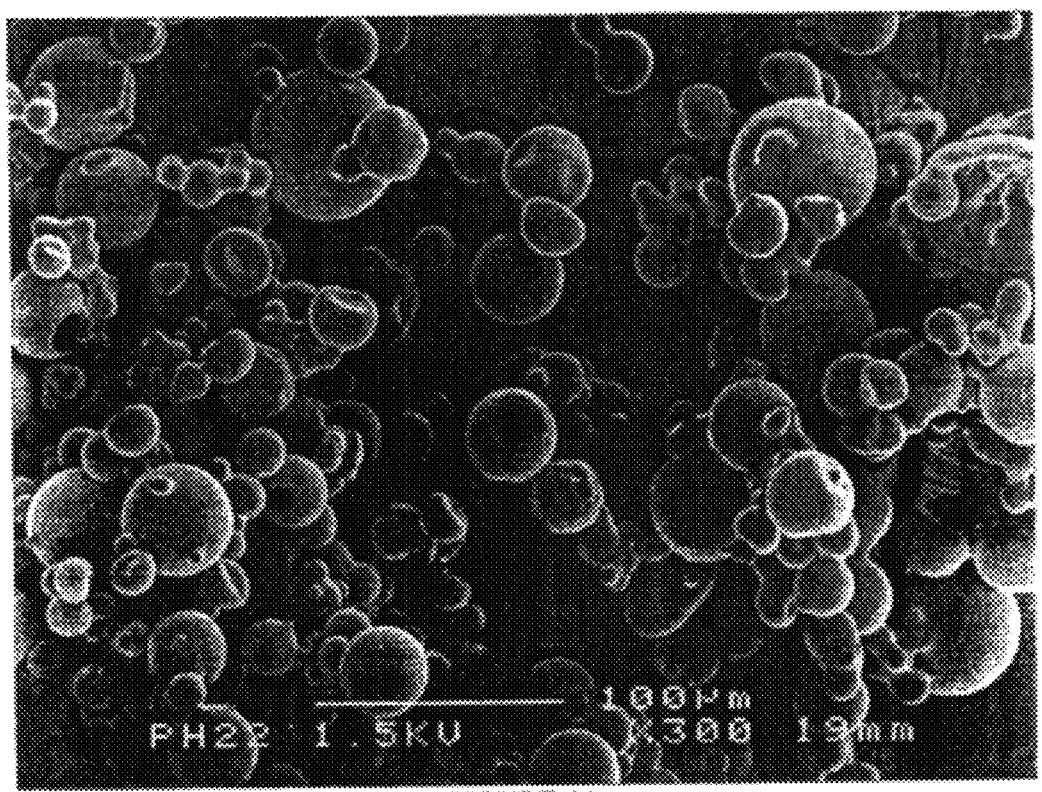
FIGS. 4A–4B depict scanning electron micrographs of powder samples dispersed in paraffin oil at 300× magnification (3A) and 2000×magnification (3B).
Figure 4B:
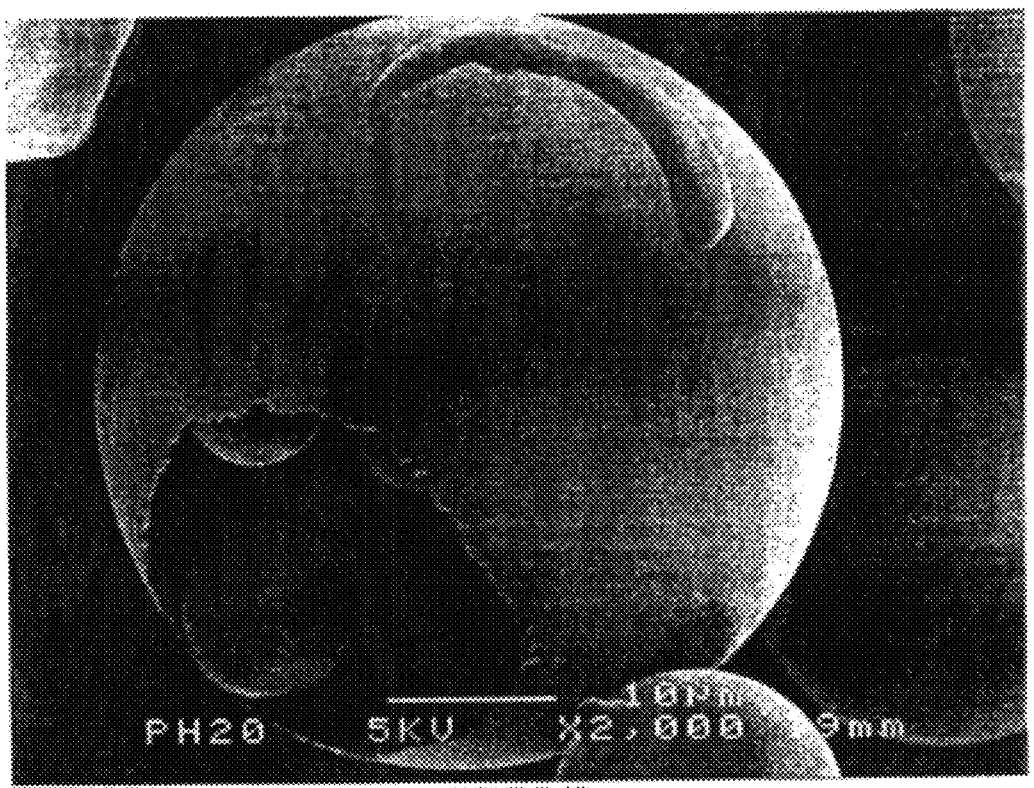

A larger particle size, resulting in better flow properties as in sample B, can be obtained by agglomeration. FIG. 2 shows the typical structure of an agglomerated powder (sample B, magnification ×400).

The true, bulk and tap densities of the different batches are also given in table 2. The Hausner ratio of all samples is such that they are each suitable for direct compaction processes.

When the true density of the original and milled materials are compared it is obvious that there are differences in the amount of air included in the particles.

This can also be seen in FIGS. 1 (sample A, magnification ×400), 2 (sample B, magnification ×400), 3a and 3b (sample C, magnifications ×300 and ×2000) and 4a and 4b (sample D, magnifications ×300 and ×2000). FIGS. 1 and 2 are light microscopy pictures of powder samples dispersed in paraffin oil. Pores and vacuoles are visible as black areas. FIGS. 3a, 3b, 4a and 4b are SEM pictures. FIG. 1 shows agglomerates with a porous structure without large vacuoles. FIG. 2 shows agglomerates made up of single particles with large vacuoles. Due to the high cristallinity of this product the surface of the particles shows rough. In FIGS. 3a, 3b, 4a and 4b due to explosion of some particles the hollow structure of the single powder particles can be seen.

TABLE 2

Flow properties and densities

| Batch Number | Flow* [mm] | Bulk density [g/cm$^3$] | Tap density [g/cm$^3$] | Hausner ratio | Density** [g/cm$^3$] |
|---|---|---|---|---|---|
| A | >18 | 0.43 | 0.53 | 1.23 | 1.441 |
| B | 5 | 0.38 | 0.49 | 1.29 | 1.300 |
| C | >18 | 0.46 | 0.52 | 1.13 | 1.26 |
| D | >18 | 0.45 | 0.60 | 1.33 | 1.11 |

*: the flow is expressed as the minimum aperture through which the powder was free flowing.
**: (true) density of the original material without milling.

Compaction Properties

In table 3 the crushing strengths of compacts from the different inulin and lactose samples are presented.

As a reference for sample D the crushing strengths of a commercially available spray dried lactose (Pharmatose® DCL 11) are integrated in this table as sample E. Data were extracted from G. K. Bolhuis and Z. T. Chowhan, "Materials for direct compaction", in "Pharmaceutical compaction technology", Eds. G. Alderborn and C. Nyström, Marcel Dekker Inc., New York 1996, pp. 465.

The results clearly show that the different samples exhibit varying compaction properties. On the other hand, the results of the unlubricated tablets demonstrate that all different types of inulin as such have excellent binding properties upon compaction (crushing strengths all above 60 N). So irrespective of its crystallinity, inulin exhibits a high bonding capacity. Sample D shows unlubricated high crushing strengths compared with sample E. The differences found for lubricated and unlubricated tablets show that there is a significant effect of the magnesium stearate. Especially the lubricant sensitivity ratio (L.S.R.) for the sample A is very high, whereas it is high for the sample E. For this sample A it is found that although the crushing strengths measured for unlubricated material is quite sufficient, the crushing strength for the lubricated materials is clearly insufficient. As described in the methods section, the experiments were done at a high compaction speed to mimic the behavior of the powders on high speed tabletting machines. At lower compaction speed the lubricant sensitivity ratio was lower (data not shown). However, since most pharmaceutical companies use high speed tabletting machines, high compaction speed values are relevant. It is clear that samples B, C and D show a superior lubricant sensitivity ratio.

TABLE 3

Compaction force, crushing strength, porosity and lubricant, sensitivity off tablets

| Batch Number | Force [kN] | Crushing strength [N] unlubricated | lubricated | Porosity [%] Unlubricated | Lubricated | L.S.R. |
|---|---|---|---|---|---|---|
| A | 20 | 174 | 44 | 16.4 | 16.8 | 0.75 |
|   | 30 | 201 | 60 | 11.3 | 9.4 | 0.70 |
| B | 20 | 151 | 160 | 16.1 | 16.4 | −0.06 |
|   | 30 | 267 | 278 | 9.0 | 9.5 | −0.04 |
| C | 20 | 270 | 230 | 16.4 | 17.2 | 0.15 |
| D | 20 | 200 | 190 | 11.8 | 12.6 | 0.05 |
| E | 20 | 155 | 90* | — | — | 0.42 |
|   | 30 | 160 | 115* | — | — | 0.28 |

*Lubricated with 1% magnesium stearate

Tablet Properties

All inulin samples studied show sufficient binding to serve as a filler-binder in direct compaction processes. For further evaluation of these samples, tablets of 500 mg were prepared with a compaction force of 25 kN. In table 4 the characteristics of these tablets are presented. During the disintegration tests it was found for both samples tested that the tablets dissolved. The disintegration time of tablets of sample B was extremely long. This can be explained by the high mean degree of polymerization and the crystallinity of this material. The disintegration time of this sample however could be reduced by adding a disintegrant. The crushing strength and resistance to friability of sample A was poor, especially for the lubricated tablets.

TABLE 4

Tablet properties of flat faced inulin tablets (500 mg) compacted at 25 kN compression force.

| Batch Number | Crushing strength [N] unlubricated | lubricated | Disintegration time [sec] Unlubricated | lubricated | Friability [%] Lubricated |
|---|---|---|---|---|---|
| A | 172 | 52 | 339 | 473 | 2.2 |
| B | 205 | 220 | >1800 | >1800 1020* | 0.6 |

*with 4% sodium starch glycolate

What is claimed is:
1. A filler-binder for a tablet in the form of hollow particles, each particle comprising a hollow space, wherein the volume of the space is at least 30% of the volume of the particle, and wherein the filler-binder comprises a water-soluble material.
2. A filler binder according to claim 1, wherein the volume of the space is at least 50% of the volume of the particle.
3. A filler-binder according to claim 1, wherein the particles have a diameter between 25 and 1000 μm.
4. A filler-binder according to claim 1, comprising agglomerates of the hollow particles.
5. A filler binder according to claim 1, wherein the volume of the space is at least 60% of the volume of the particle.
6. A filler-binder according to claim 1 formed of a material having a glass transition temperature of at least 50° C.
7. A filler-binder according to claim 1 formed of a polyol, an inorganic salt or a mono-, di-, oligo- or polysaccharaide.
8. A filler-binder according to claim 7 formed of a fructan or a derivative thereof.
9. A filler-binder according to claim 8, wherein the fructan is inulin.
10. A process for producing a tablet wherein a dry mixture comprising a filler-binder according to claim 1, a lubricant, and an active ingredient, is formed into a tablet by compaction.
11. A tablet obtainable by a process according to claim 10.
12. A tablet according to claim 11 further comprising one or more conventional additives.
13. A process for preparing a filler-binder according to claim 1 wherein hollow particles are produced by spray drying a solution or suspension of the filler-binder with injection of a gas.
14. A tablet according to claim 12, wherein the additive is a disintegrant.

* * * * *